(12) United States Patent
Hammond

(10) Patent No.: US 6,312,927 B1
(45) Date of Patent: Nov. 6, 2001

(54) METHODS FOR PRODUCING NUCLEIC ACIDS LACKING 3'-UNTRANSLATED REGIONS AND OPTIMIZING CELLULAR RNA-PROTEIN FUSION FORMATION

(75) Inventor: Philip W. Hammond, Ayer, MA (US)

(73) Assignee: Phylos, Inc., Lexington, MA (US)

( * ) Notice: Subject to any disclaimer, the term of this patent is extended or adjusted under 35 U.S.C. 154(b) by 0 days.

(21) Appl. No.: 09/374,962

(22) Filed: Aug. 16, 1999

Related U.S. Application Data

(60) Provisional application No. 60/096,818, filed on Aug. 17, 1998.

(51) Int. Cl.[7] .............................. C12Q 1/68; C12P 19/34
(52) U.S. Cl. .................................. 435/91.1; 435/5; 435/6; 435/91.2
(58) Field of Search .................................. 435/5, 6, 91.1, 435/91.2

(56) References Cited

U.S. PATENT DOCUMENTS

| | | | |
|---|---|---|---|
| 5,627,024 | 5/1997 | Maruyama et al. | 435/5 |
| 5,643,768 | 7/1997 | Kawasaki | 435/91.21 |
| 5,789,208 | 8/1998 | Sharon | 435/91.41 |
| 5,849,878 | 12/1998 | Cantor et al. | 530/391.9 |
| 5,965,133 | 10/1999 | Cantor et al. | 424/179.1 |
| 5,985,575 | 11/1999 | Wickens et al. | 435/6 |

FOREIGN PATENT DOCUMENTS

| | | |
|---|---|---|
| WO 98/31700 | 7/1998 | (WO) . |
| WO 99/51773 | 10/1999 | (WO) . |

OTHER PUBLICATIONS

Capecchi, "Polypeptide Chain Termination In Vitro: Isolation of a Releasable Factor," Proc. Natl. Acad. Sci. 58:1144–1151 (1967).

Capecchi and Klein, "Release Factors Mediating Termination of Complete Proteins," Nature 226:1029–1033 (1970).

Drugeon et al., "Eukaryotic Release Factor 1 (eRF1) Abolishes Readthrough and Complete with Suppressor tRNAs at all Three Termination Codons in Messenger RNA," Nucl. Acids Res. 25:2254–2258 (1997).

Frolova et al., "A Highly Conserved Eukaryotic Protein Family Possessing Properties of Polypeptides Chain Release Factor," Nature 372:701–703 (1994).

Frolova et al., "Eukaryotic Polypeptide Chain Release Factor eRF3 is an eRF1–and Ribosome–Dependent Guanosine Triphosphatase," RNA 2:334–341 (1996).

Frolova et al., "Mammalian Polypeptide Chain Release Factor and Tryptophanyl–tRNA Synthetase are Distinct Proteins," The EMBO Journal 12:4013–4019 (1993).

Higuchi, "Using PCR to Engineer DNA," Stockton Press, Chapter 6, pp. 61–70, 1989.

Ilan, "Releasing Factor Regulating Termination of Complete Protein in a Eukaryotic Organism," J. Mol. Biol. 77:437–448 (1973).

Kisselev and Frolova, "Termination of Translation in Eukaryotes," Biochem. Cell Biol. 73:1079–1086 (1995).

Miyamoto–Sato et al., "Specific Bonding of Puromycin to Full–Length Protein at the C–Terminus," Nucl. Acids Res. 28:1176–1182 (2000).

Roberts et al., "RNA–Peptide Fusions for the vitro Selection of Peptides and Proteins," Proc. Natl. Acad. Sci. USA, 94:12297–12302, 1997.

(List continued on next page.)

Primary Examiner—Jezia Riley
(74) Attorney, Agent, or Firm—Clark & Elbing LLP

(57) ABSTRACT

Described herein are methods for removing the 3'-untranslated regions from cDNA or mRNA molecules, as well as methods for the use of such products for RNA-protein fusion formation.

11 Claims, 14 Drawing Sheets

OTHER PUBLICATIONS

Singer et al., "Libraries for Genomic SELEX," Nucl. Acids Res. 25:781–786 (1997).

Stansfield et al., "The Products of the SUP45 (eRF1) and SUP35 Genes Interact to Mediate Translation Termination in Saccharomyces Cerevisiae," The EMBO J. 14:4365–4373 (1995).

Stansfield et al., "Depletion in the Levels of the Release Factor eRF1 Causes a Reduction in the Efficiency of Translation Termination in Yeast," Mol. Microbiol. 20:1135–1143 (1996).

Zhouravleva et al., "Termination of Translation in Eukaryotes is Governed by Two Interacting Polypeptide Chain Release Factors, eRF1 and eRF3," The EMBO J. 14:4065–4072 (1995).

Zozulya et al., "Mapping Signal Transduction Pathways by Phage Display," Nature Biotech. 17:1193–1198 (1999).

Niemeyer et al., "Oligonucleotide–Directed Self–Assembly of Proteins: Semisynthetic DNA—Streptavidin Hybrid Molecules as Connectors for the Generation of Macroscopic Arrays and the Construction of Supramolecular Bioconjugates," Nucl. Acid Res. 22:5530–5539 (1994).

Fig. 14

| Label | Left sequence | Right sequence |
|---|---|---|
| T5-tr | GTGTATGGGTTGTTTATG | ACAATTTATGAAATGACG |
| Myeloid Differentiation factor | GCGTATGGGTTGTTTATG | ACAATTTATGAAATACAG |
| B40-tr | AAAGTTGTTCAAGTTTAT | CCAGAGTTTGGGCAGAAG |
| Transcription intermediary factor | AAAGTTGTTCAAGTTTAT | CCAGAGTTTGAGAGGAAA |
| B31-tr | GGTAACACAGAGGAAA | GATATTGTCCTGGATGTA |
| β-COP homologue | GGTAACACAGAGGAAA | GATATTGTCCGGGATGGA |
| T23-tr | TTGGTTTTTGGATGAAGCT | AGGTACCTGCCTCCAGCC |
| KIAA0111 | TTGGTTTTTGGATGAAGCT | AGGTACCTGCCTCCAGCC |
| B32-tr | GGTGAGAGACCTACACC | GATCCTGATTTACACACC |
| KIAA0673 | GGTGGAGAGACCTACACC | GATCCTGATCTACAT-CA |
| M15-tr | GGTCTTCTATTTTACCCCC | ACAGGCTTCCACGGACAT |
| Cytochrome C Oxidase | GGTCTTCTATTTTACCCTC | ACAGGCTTCCACGGACTT |

N(9) ↑ ........ N(9) ↓

METHODS FOR PRODUCING NUCLEIC ACIDS LACKING 3'-UNTRANSLATED REGIONS AND OPTIMIZING CELLULAR RNA-PROTEIN FUSION FORMATION

CROSS REFERENCE TO RELATED APPLICATIONS

This application claims the benefit of the filing date of application, Ser. No. 60/096,818, filed Aug. 17, 1998 now abandoned.

BACKGROUND OF THE INVENTION

In general, the invention features methods for modifying nucleic acid substrates, for example, for the production of RNA-protein fusions.

Covalently bonded RNA-protein fusions may be used in methods for generating or isolating proteins with desired properties from pools of proteins. To create such fusions, an RNA and the peptide or protein that it encodes may be joined during in vitro translation using synthetic RNA that carries a peptidyl acceptor, such as puromycin, at its 3'-end (Roberts & Szostak (1997) Proc. Natl. Acad. Sci. USA 94, 12297–12302). In this process, the synthetic RNA, which is devoid of stop codons, is typically synthesized by in vitro transcription from a DNA template followed by 3'-ligation to a DNA linker carrying puromycin. The DNA sequence causes the ribosome to pause at the end of the open reading frame, providing additional time for the puromycin to accept the nascent peptide chain and resulting in the production of the RNA-protein fusion molecule.

SUMMARY OF THE INVENTION

The present invention involves methods for optimizing the production of RNA-protein fusions beginning with cellular RNA or other nucleic acids having 3'-untranslated regions. As described in more detail below, such fusions may be generated by at least two general techniques. According to one general approach, nucleic acids are produced which lack both 3'-untranslated regions and poly A tails. These nucleic acids, which may also lack a terminal stop codon, are then used for the production of RNA-protein fusions. According to the second technique, rather than modifying the nucleic acid substrate, the fusion is generated in an in vitro translation reaction mixture which lacks functional translation release factors. The absence of these factors circumvents the problem of termination at terminal stop codons (or other stop codons inadvertently introduced into a protein coding sequence) and allows for the generation of RNA-protein fusions. The invention also encompasses methods in which these two general approaches are combined for the purpose of RNA-protein fusion formation and methods in which the approaches, singly or in combination, are used for other purposes in which nucleic acids lacking 3'-terminal sequences or translation through stop codons are useful or desirable.

Accordingly, in a first aspect, the invention features a method for removing the 3'-untranslated region of a DNA molecule including an open reading frame, the method involving: (a) providing a DNA molecule having an open reading frame and a 3'-untranslated region, the DNA molecule terminating at its 5' end in an overhang and at its 3' end in a blunt end; and (b) treating the DNA molecule first with a 3'→5' exonuclease and then with a single-stranded nuclease under conditions that allow removal of the 3'-untranslated region.

In preferred embodiments, the 3'→5' exonuclease is exonuclease III; the nuclease is Mung bean nuclease; step (b) further results in removal of the stop codon of the open reading frame; the DNA molecule is a cDNA produced by reverse transcription from an mRNA sequence; and the method is carried out on a population of DNA molecules.

In a related aspect, the invention features a method for removing the 3'-untranslated region of an mRNA molecule, the method involving: (a) translating an mRNA molecule in vitro in a translation reaction mixture lacking functional translation release factor activity, resulting in pausing of the translation reaction mixture ribosomes at the stop codon of the mRNA molecule; (b) adding, to the translation reaction mixture of step (a), reverse transcriptase and an oligonucleotide primer which is complementary to the 3'-untranslated region of the mRNA molecule at a site proximal to the stop codon, under conditions which allow the synthesis of a strand of DNA that is complementary to the 3'-untranslated region and terminates at a site proximal to the stop codon; and (c) removing the RNA portion of the RNA-DNA duplex formed in step (b), thereby removing the 3'-untranslated region of the mRNA molecule.

In preferred embodiments, the oligonucleotide primer comprises a poly T sequence; step (c) is carried out by treatment of the product of step (b) with RNaseH; the method is carried out on a population of mRNA molecules; and the method further involves the steps of: (d) ligating to the 3' end of the product of step (c) a linker including a Type IIS restriction site; (e) extending the product of step (d) to produce a double-stranded DNA molecule; and (f) treating the double-stranded DNA molecule with the Type IIS restriction enzyme to cleave the DNA molecule and remove the stop codon.

In another related aspect, the invention features a method for removing the 3'-untranslated regions and stop codons of a population of mRNA molecules, the method involving: (a) providing a population of mRNA molecules; (b) synthesizing strands of DNA, each of which is complementary to one of said mRNA molecules, using a random primer mixture, the random primer mixture including primers, each having (i) a 3' region including a stop codon flanked by a random oligonucleotide located 3', 5', or both to the stop codon; and (ii) a 5' region including a Type IIS restriction site; (c) ligating to the 3' ends of the DNA products of step (b) an oligonucleotide tail; (d) amplifying the products of step (c) using (i) a first primer which is complementary to the Type IIS restriction site-containing sequence; and (ii) a second primer which is complementary to the oligonucleotide tail; and (e) treating the products of step (d) with the Type IIS restriction enzyme to cleave the products, thereby removing the 3'-untranslated regions and stop codons.

In preferred embodiments, the second primer of step (d) further includes a 5' region including an RNA polymerase recognition site; and the method further comprises: (f) ligating a sequence which encodes an affinity tag to the cleaved ends of the products of step (e); (g) transcribing the products of step (f); (h) ligating peptidyl acceptors to the 3' ends of the RNA products of step (g); (i) translating the products of step (h) to produce a population of RNA-protein fusions; and (j) substantially isolating RNA-protein fusions which comprise the affinity tag, thereby obtaining a population of mRNA molecules lacking 3'-untranslated regions and stop codons.

In yet another related aspect, the invention features a method for removing the 3'-untranslated regions and stop codons of a population of mRNA molecules, involving: (a)

providing a population of mRNA molecules; (b) synthesizing strands of DNA, each of which is complementary to one of the mRNA molecules, using a random primer mixture, the random primer mixture including primers, each having (i) a 5' region which lacks a stop codon in at least one reading frame and (ii) a random 3' region; and (c) synthesizing strands of DNA complementary to the DNA strands of step (b), using a second random primer mixture.

In preferred embodiments, the second random primer mixture includes primers, each having (i) a 5' region which includes a translation start site and (ii) a random 3' region; and wherein said method further involves (d) amplifying the product of step (c) using a first amplification primer having (i) a 5' sequence which includes an RNA polymerase recognition site and (ii) a 3' region which is complementary to the translation start site.

In other preferred embodiments of each of the above two aspects, the RNA polymerase recognition site is a T7 or SP6 RNA polymerase recognition site; the affinity tag is a hexahistidine peptide, a streptavidin-binding peptide, or an epitope; the peptidyl acceptor is puromycin; and the method is carried out on a population of mRNA molecules.

In a second aspect, the invention features a method for producing an RNA-protein fusion from an mRNA having a 3'-untranslated region, the method involving: (a) covalently bonding the mRNA to a peptidyl acceptor, the peptidyl acceptor being positioned 3' of the protein coding sequence of the mRNA; and (b) translating the mRNA molecule in vitro in a translation reaction mixture lacking functional translation release factor activity.

In a related aspect, the invention features a method for producing an RNA-protein fusion from a nucleic acid having a 3'-untranslated region, the method involving: (a) providing the DNA product obtained above lacking a 340-untranslated region; (b) transcribing the DNA to produce RNA lacking a 3'-untranslated region; (c) covalently bonding to the RNA a peptidyl acceptor, the peptidyl acceptor being positioned 3' of the protein coding sequence of the RNA; and (d) translating the product of step (c) to produce an RNA-protein fusion.

In preferred embodiments, the DNA product lacks a stop codon; and the translating step is carried out in vitro in a translation reaction mixture lacking functional translation release factor activity.

In another related aspect, the invention features a method for producing an RNA-protein fusion from a nucleic acid having a 3'-untranslated region, the method involving: (a) providing the RNA product obtained above lacking a 3'-untranslated region; (b) covalently bonding to the RNA a peptidyl acceptor, the peptidyl acceptor being positioned 3' of the protein coding sequence of the RNA; and (c) translating the product of step (b) to produce an RNA-protein fusion.

In a third aspect, the invention features a library of nucleic acid molecules, each molecule including an open reading frame and lacking the 3'-untranslated region normally associated with the open reading frame.

In preferred embodiments, the nucleic acid is DNA or RNA (for example, messenger RNA or cellular RNA derived, for example, from a eukaryotic organism, such as a mammal, and, for example, a human); the library includes at least $10^5$ members; and the nucleic acid molecules of the library also lack stop codons.

In final related aspects, the invention features libraries of nucleic acid molecules and RNA-protein fusions produced by the methods of the invention.

As used herein, by a "population" is meant more than one molecule. Preferably, a population includes at least 10 molecules, more preferably, at least $10^2$ or $10^3$ molecules, and, most preferably, at least $10^4$, $10^5$, or $10^6$ molecules.

Similarly, a "library" is also any group of molecules. A library includes at least 10, preferably, at least $10^2$ or $10^3$, and, most preferably, at least $10^4$, $10^5$, or $10^6$ molecules.

By a "protein" is meant any two or more naturally occurring or modified amino acids joined by one or more peptide bonds. "Protein" and "peptide" are used interchangeably herein.

By "RNA" is meant a sequence of two or more covalently bonded, naturally occurring or modified ribonucleotides. One example of a modified RNA included within this term is phosphorothioate RNA.

By "DNA" is meant a sequence of two or more covalently bonded, naturally occurring or modified deoxyribonucleotides.

By "covalently bonded" to a peptidyl acceptor is meant that the peptidyl acceptor is joined either directly through a covalent bond or indirectly through another covalently bonded sequence (for example, DNA corresponding to a pause site).

By a "peptidyl acceptor" is meant any molecule capable of being added to the C-terminus of a growing protein chain by the catalytic activity of the ribosomal peptidyl transferase function. Typically, such molecules contain (i) a nucleotide or nucleotide-like moiety (for example, adenosine or an adenosine analog (di-methylation at the N-6 amino position is acceptable)), (ii) an amino acid or amino acid-like moiety (for example, any of the 20 D- or L-amino acids or any amino acid analog thereof (for example, O-methyl tyrosine or any of the analogs described by Ellman et al., Meth. Enzymol. 202:301, 1991), and (iii) a linkage between the two (for example, an ester, amide, or ketone linkage at the 3' position or, less preferably, the 2' position); preferably, this linkage does not significantly perturb the pucker of the ring from the natural ribonucleotide conformation. Peptide acceptors may also possess a nucleophile, which may be, without limitation, an amino group, a hydroxyl group, or a sulfhydryl group. In addition, peptidyl acceptors may be composed of nucleotide mimetics, amino acid mimetics, or mimetics of the combined nucleotide-amino acid structure.

Other embodiments of the invention will be apparent from the detailed description thereof, and from the claims.

BRIEF DESCRIPTION OF THE DRAWINGS

FIG. 14 is a diagram illustrating the sequence of clones selected from an RNA-protein fusion library derived from cellular RNA and which lack both stop codons and 3' untranslated regions. In each pair of sequences, the first line is the clone sequence from the fusion library, and the second line is the parent RNA sequence. The shaded regions correspond to the $N_9$ portion of the primers.

DETAILED DESCRIPTION

As discussed above, the present invention provides two general approaches for the modification or use of nucleic acids having 3'-untranslated regions for the production of RNA-protein fusions, or any other technique where stop codons or untranslated regions are undesirable.

In the first approach, mRNA or cDNA libraries are created that lack 3' untranslated regions and poly A tails, and, if desired, also lack 3'-terminal stop codons. Such cDNAs are greatly improved compared to traditional cDNA libraries since they are enriched for coding sequence information. In addition, creation of these cDNA libraries enables the creation of libraries of cellular mRNA molecules covalently linked to the protein molecules the mRNAs encode. Such "fusion libraries" can be used for a variety of applications, including the identification of protein-protein interactions, identification of drug targets, and hybridization to solid supports to create, for example, protein chips (or beads); if desired, the RNA-protein molecules may be arranged in spatially defined arrays on such chips to carry out large scale screening, for example, for protein or compound identification. Exemplary uses for RNA-protein fusions are described, for example, in Roberts & Szostak (1997) Proc. Natl. Acad. Sci. USA 94, 12297–12302; Szostak et al., Selection of Proteins Using RNA-Protein Fusions, U.S. Ser. No. 09/007,005, Jan. 14, 1998 and U.S. Ser. No. 09/247,190, Feb. 9, 1999; and Kuimelis et al., Addressable Protein Arrays, U.S. Ser. No. 60/080,686, Apr. 3, 1998, and U.S. Ser. No. 09/282,734, Mar. 31, 1999.

The second approach of the invention focuses on overcoming the natural translational termination which is brought about by the interaction between the stop codon at the 3' end of an mRNA coding sequence and the release factors present in a translation lysate. To circumvent this obstacle, stop codons are removed from the mRNA molecule (as described above) or the release factor activity is removed from the in vitro translation system. By either of these strategies, translation results in mRNA-polypeptide-ribosome complexes which are suitable substrates for the formation of mRNA-protein fusions. Again, this approach simplifies fusion formation beginning with natural mRNA messages which contain stop codons and also simplifies the use of such fusion technology for such applications as functional genomics.

Exemplary methods for carrying out the general approaches of the invention are now described below. These examples are provided for the purpose of illustrating, and not limiting, the invention.

EXAMPLE 1

Nucleic Acid Sequence Modification Approaches

In a first approach, the termination of translation is avoided by removing the region of an mRNA which contains a stop codon, while preserving as much of the mRNA coding sequence as possible. Four alternative ways of modifying the mRNA coding sequence are presented below.

Figure 1:
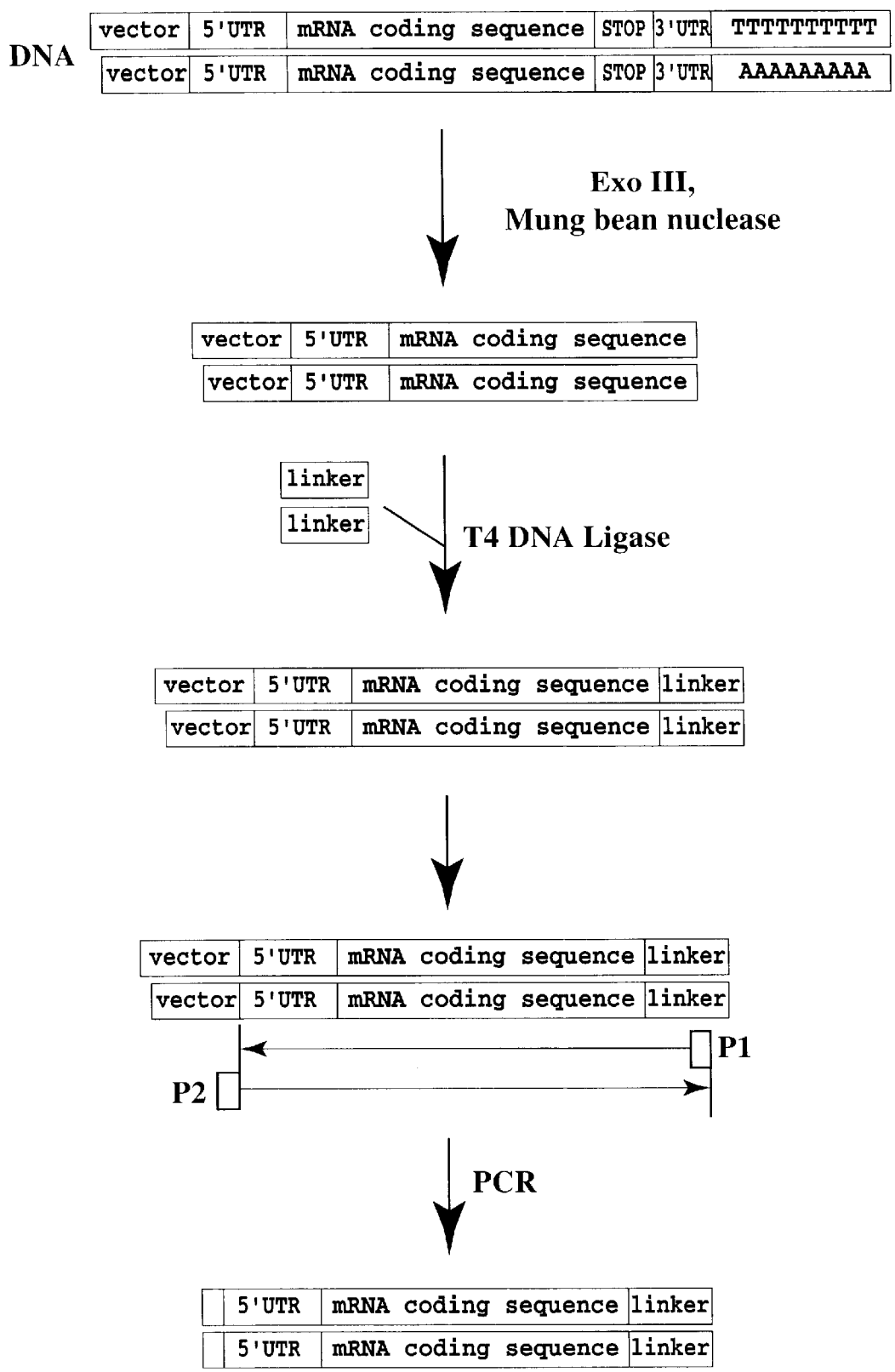
FIG. 1 is a schematic illustration of one exemplary approach for removing the 3'-untranslated region and poly A tail from a nucleic acid molecule.

FIG. 1 shows a first mRNA modification technique in which the coding sequence is modified at the DNA level. The coding regions of a cDNA library are excised from host vectors in such a way that the sequence upstream of the coding sequence terminates in a single 3' DNA chain overhang of at least four bases, whereas the sequence downstream of the coding sequence terminates in a blunt cut. This may be accomplished by the use of appropriate restriction enzymes (in combination, for example, with vectors containing useful restriction sites) and standard molecular biology techniques. Exonuclease III and Mung bean nuclease are then used sequentially (with exonuclease III being used first and Mung bean nuclease being used second) to remove nucleotides from the unprotected, downstream end of the cDNA clone. The length of incubation with exonuclease III is adjusted by standard techniques such that the cDNA polyadenosine tail, 3' untranslated region, and (if desired) stop codon, but little of the coding sequence, are removed. In an alternative technique, S1 nuclease may be used in place of Mung bean nuclease, again adjusting the incubation time to allow removal of the 3'-untranslated region but little or none of the coding sequence.

For use in RNA-protein fusion formation, a defined DNA sequence may then be ligated to the newly created downstream end, creating the ideal substrate for in vitro transcription and translation. This DNA sequence is complementary to a splint sequence that is used to facilitate the ligation of a peptidyl acceptor to the mRNA product of the modified DNA upon transcription. Exemplary sequences and methods for in vitro transcription, in vitro translation, and fusion formation are described, for example, in Roberts & Szostak (1997) Proc. Natl. Acad. Sci. USA 94, 12297–12302; and Szostak et al., U.S. Ser. No. 09/007,005 and U.S. Ser. No. 09/247,190. These sequences may be joined to the RNA molecule using, for example, T4 DNA ligase. The resulting RNA substrate may be used directly in in vitro transcription and in vitro translation steps or, as shown in FIG. 1, may be amplified (for example, by standard PCR amplification) to generate a library of cDNA molecules lacking 3'-untranslated regions.

Figure 2:
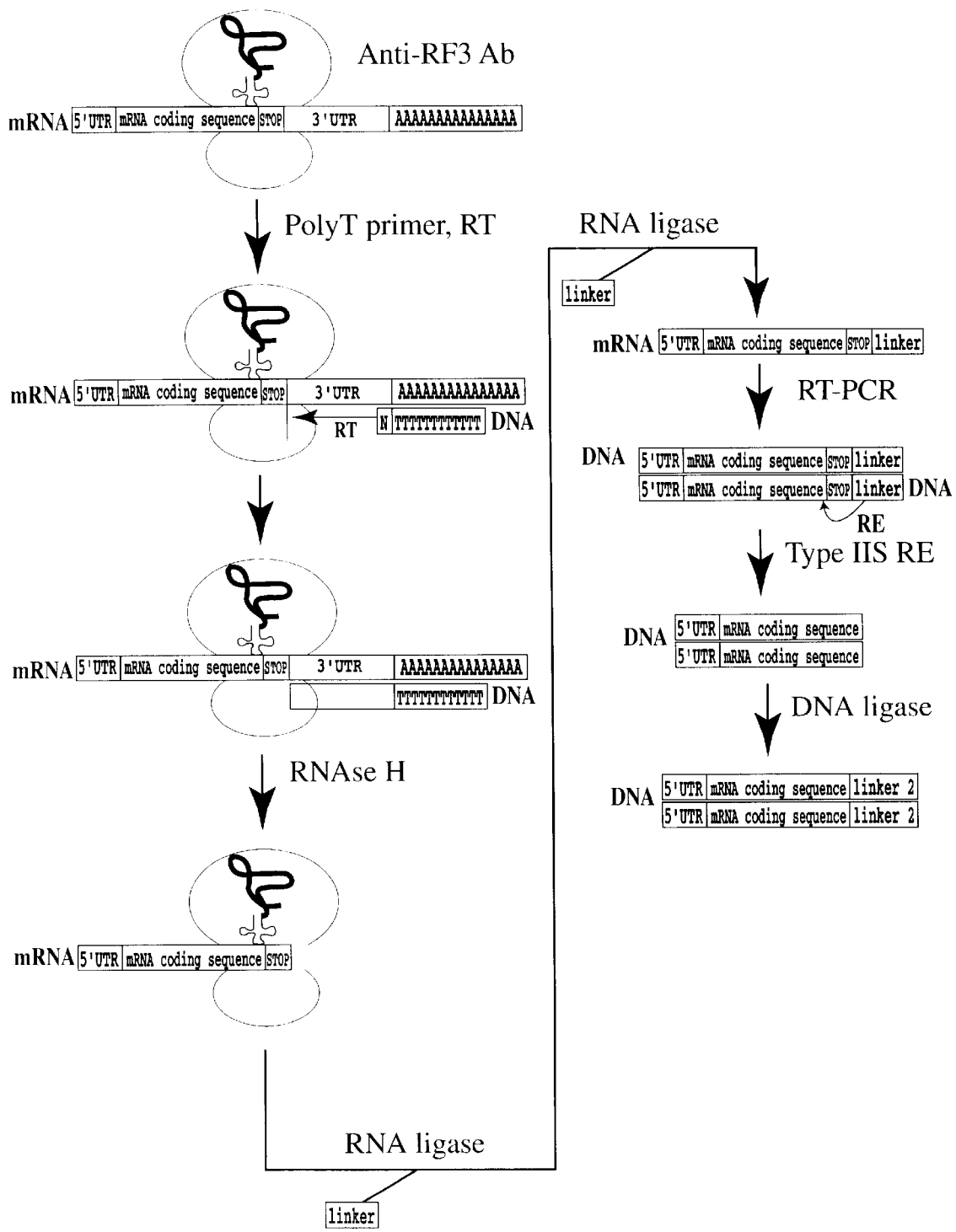
FIG. 2 is a schematic illustration of a second exemplary approach for removing the 3'-untranslated region and poly A tail from a nucleic acid molecule.

In a second approach (shown in FIG. 2), cDNA clones are transcribed in vitro into mRNA molecules which contain stop codons, untranslated 3' regions, and polyadenosine tails. Alternatively, mRNA may be isolated from cells and used directly. The mRNA is then subjected to in vitro translation by any standard technique in the presence of inhibitors of translation release factors (see below). Under such reaction conditions, ribosomes do not release the polypeptide chain upon reaching the stop codon, but instead pause. A DNA oligonucleotide primer complementary to the polyA tail (that is, a poly T sequence preferably of a length of between 10–30 nucleotides) and reverse transcriptase are then added to the mix, resulting in the synthesis of a strand of DNA complementary to the downstream region of the mRNA which terminates in the region proximal to the stop codon. RNaseH is then used to remove the RNA portion of the RNA-DNA region.

The RNA product may then be used to generate cDNA libraries or for RNA-protein fusion formation. To create cDNA libraries (lacking 3' untranslated regions), an adaptor molecule is preferably ligated to the RNA to create a defined sequence on the 3' end using T4 RNA ligase. This adaptor is a short, double-stranded piece of DNA (preferably, between 10–50 base pairs in length) with a sequence designed to facilitate further processing of the cDNA library. The adaptor is used as the basis for complementary PCR primers for cDNA library construction, or as "splint" oligonucleotides to facilitate the ligation of RNA products to peptidyl acceptor-containing linkers, as described below.

Primers are then used in combination with standard cDNA construction methodologies to create cDNA libraries. Alternatively, to generate RNA-protein fusions, a linker sequence may be ligated onto the 3' end of the RNA with either T4 RNA or T4 DNA ligase, where the 3' end of the linker contains a peptidyl acceptor, such as puromycin (see, for example, Roberts & Szostak (1997) Proc. Natl. Acad. Sci. USA 94, 12297–12302; and Szostak et al., Selection of Proteins Using RNA-Protein Fusions, U.S. Ser. No. 09/007, 005, Jan. 14, 1998, and U.S. Ser. No. 09/247,190, Feb. 9, 1999). This RNA-linker-puromycin construct may then be used directly for in vitro translation in a lysate depleted of release factors to generate RNA-protein fusion molecules.

Alternatively, to remove the stop codon from the mRNA, a linker with a defined sequence containing an offset cutting restriction enzyme site, such as a Type IIS restriction site (for example, a BsgI, HphI, or AsuHPI restriction site), is ligated, as described above, to the region downstream of the stop codon. The RNA is then amplified, for example, by standard methods of RT-PCR, and treated with the restriction enzyme. This type of restriction enzyme cuts upstream from its recognition site, thus removing the stop codon. The DNA, which contains the coding sequence but not the stop codon, may then be used in standard protocols for transcription and formation of RNA-protein fusions (see, for example, Roberts & Szostak (1997) Proc. Natl. Acad. Sci. USA 94, 12297–12302; and Szostak et al., Selection of Proteins Using RNA-Protein Fusions, U.S. Ser. No. 09/007, 005, Jan. 14, 1998, and U.S. Ser. No. 09/247,190, Feb. 9, 1999).

Figure 3:
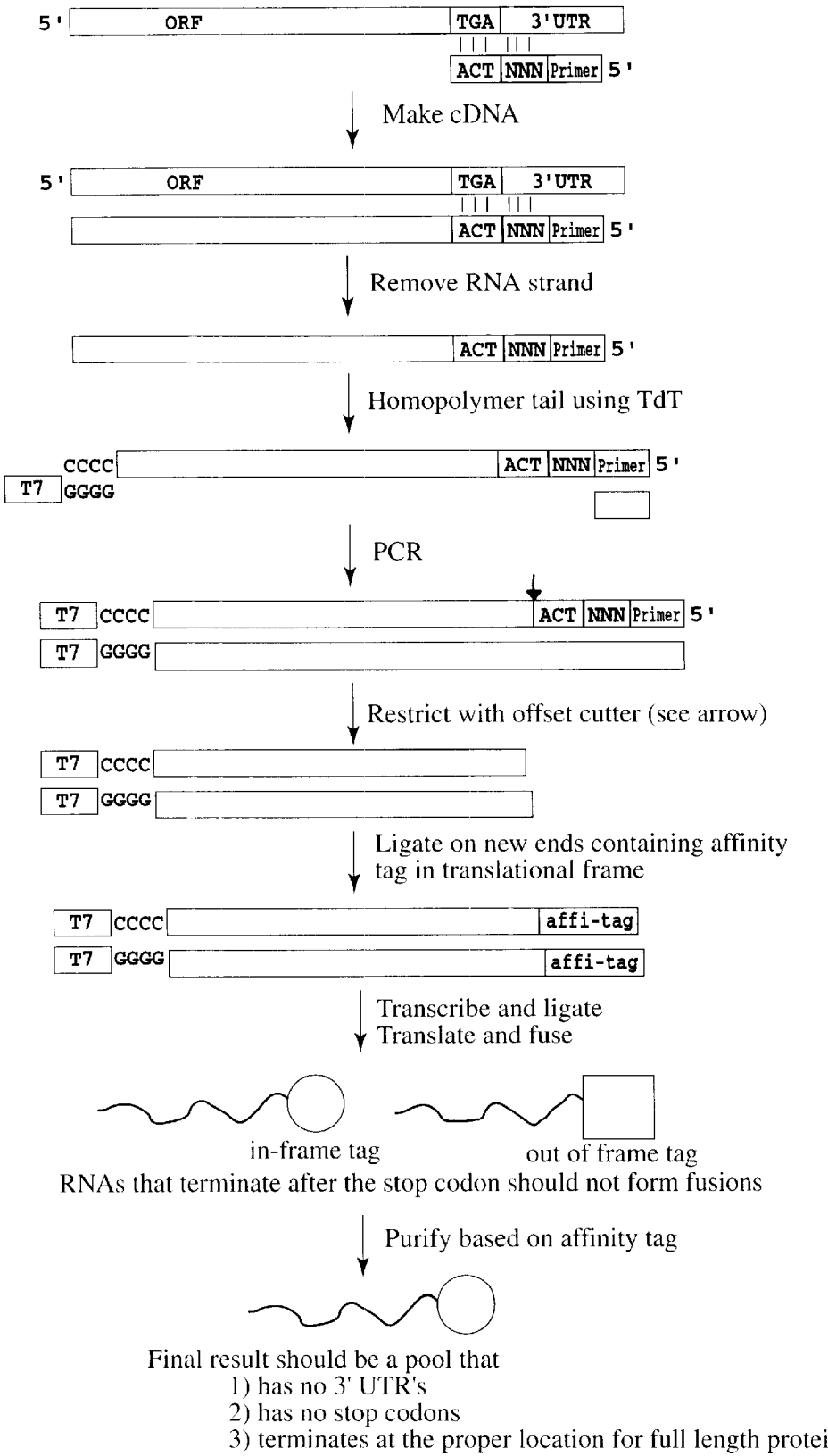
FIG. 3 is a schematic illustration of a third exemplary approach for removing the 3'-untranslated region and poly A tail from a nucleic acid molecule.

In a third general approach, biased random priming is used to remove both 3' untranslated regions and the stop codons from the members of a cDNA library. This general approach is shown in FIG. 3. In the first step of this method, a cDNA library is made, by standard techniques, from purified cellular mRNA using a biased random primer mix. This mix includes primers with sequences complementary to each of the three stop codons (TGA, TAA, or TAG) (one stop codon per primer) in the 3' region flanked on the 3' side, 5' side, or both by an additional 1–8 nucleotide long, completely random sequence. In addition, the 5' region of the primer contains a fixed sequence corresponding to the recognition site for an offset cutting (Type IIS) restriction enzyme. Examples of Type IIS restriction enzymes include BsgI, HphI, and AsuHPI. By optimizing the stringency of annealing during cDNA synthesis, such primers will only significantly anneal to and be extended from sites corresponding to stop codons within the mRNA. These stop codon sequences are found in all three cDNA reading frames as well as in both the 3' and 5' untranslated regions.

Following cDNA synthesis, the RNA template is removed. This can be accomplished either enzymatically, for example, through the action of an RNase, or chemically, for example, by treatment at high pH (for example, a pH of at least 13). The cDNA strands are then tailed with a homopolymeric sequence using an enzyme such as terminal deoxynucleotidyl transferase (TdT). A particularly suitable tail is poly-deoxycytidine. The resulting tailed cDNA is then amplified, for example, using PCR and appropriate primer sequences. One of these primers is complementary to the conserved region of the initial primer which contained the restriction site, and the second primer contains a 5' region that includes an RNA polymerase recognition sequence (for example, a T7 or SP6 RNA polymerase recognition site) and a 3' region that is complementary to the homopolymer tail plus 1–3 terminal nucleotides containing a mix of all nucleotides. In addition, the closest of these mixed nucleotides to the homopolymer region may contain any nucleotide except G. Such a tail ensures that the primer preferentially aligns with the first few nucleotides of the poly-deoxycytidine tail.

The double-stranded PCR product is then digested with the off-set cutting Type IIS restriction enzyme. Because of the primer used in the random priming step, this restriction cut occurs upstream of the stop codon at which the initial priming event occurred. In certain situations, it may be desirable to only partially cut the PCR products, for example, if those products are known or suspected to contain one or more native internal restriction sites for the chosen enzyme. In these circumstances, the restriction conditions are adjusted such that the enzyme cuts each product, on average, only once.

After removal of the short fragments cleaved from the ends of the DNAs, new ends are ligated on. These new ends encode an affinity purification tag, for example, a hexahistidine peptide, streptavidin-binding protein, or any suitable epitope, in-frame with the initial stop codon at which cDNA synthesis was primed. This double-stranded DNA with the newly ligated 3' terminus may then be purified, if desired.

Next, using a suitable RNA polymerase (that is, one which corresponds to the RNA polymerase recognition site chosen above), the double-stranded DNA is transcribed to produce single-stranded RNA. Each of these RNA molecules has the same 3' terminus, corresponding to the ligated affinity purification tag. Additional sequence is then ligated onto the 3' ends of these RNA strands in a template-directed manner, using an enzyme such as T4 DNA ligase. This new 3' sequence is preferably poly-deoxyadenosine with a 3' terminal moiety suitable for producing nucleic acid/protein fusions, for example, a dCC-puromycin group. The ligated product is then purified and translated using any suitable in vitro translation system, for example, a rabbit reticulocyte lysate. In such a system, the ribosome pauses upon reaching the poly-deoxyadenosine region, and the dCC-puromycin group is fused to the nascent polypeptide strand. If a stop codon is encountered prior to the poly-deoxyadenosine, the ribosome is released, and no fusion occurs. This will be the case if the initial priming site occurred in the 3' untranslated region.

Nucleic acid/protein fusions are then purified using the translated affinity purification tag. If the initial site of priming was an out-of-frame stop codon, the affinity tag will be mis-translated. Therefore, by this selection, only fusions from in-frame stop codons will be present after purification.

RNA from the purified fusions is then recovered and amplified using, for example, RT-PCR. The resulting cDNA library should have only full length, in-frame mRNAs with no in-frame stop codons and no 3' untranslated regions. The RNA population may be used as described above to generate a cDNA library or directly for RNA-protein fusion formation.

To demonstrate the utility of this approach, an exemplary RNA was chosen as a model system. This mRNA encoded the human cytochrome oxidase IV subunit A. The particular RNA that was used (FIG. 4) was generated by transcription from a PCR fragment and contained a 42 nucleotide 5' UTR, a 501 nucleotide open reading frame (ORF), and a 124 nucleotide 3' UTR. There were a total of 19 stop codons contained within the RNA: one authentic, one in the 5' UTR, 14 out of frame in the open reading frame, and three in the 3' UTR. This RNA also contained an internal restriction site for the Type IIS restriction enzyme used in the method, thereby representing a realistic model for cellular mRNA populations.

To carry out this technique, first strand cDNA synthesis was performed using a mix of primers that contained (5' to 3') the recognition sequence for the Type IIS restriction endonuclease, Bpm I, followed by six random nucleotides and, at the 3' terminus, three nucleotides complementary to the human stop codons. These primers are shown below (SEQ ID NOS: 1–3; N denotes a mix of all four nucleotides dG/dA/dC/dT):

5'-GCT TGC TGG AGT GCG AGT NNN NNN CTA
5'-GCT TGC TGG AGT GCG AGT NNN NNN TTA
5'-GCT TGC TGG AGT GCG AGT NNN NNN TCA.

Figure 5:
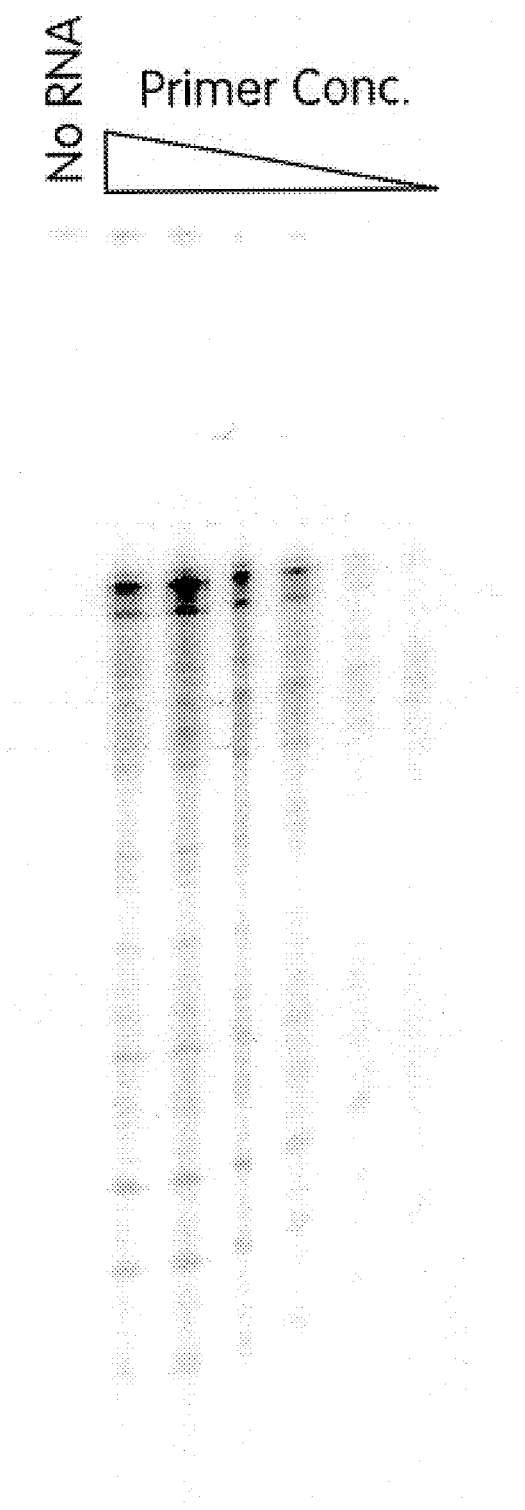
FIG. 5 is a photograph illustrating the products of first strand cDNA synthesis of the mRNA of FIG. 4, run on a denaturing polyacrylamide gel. As expected, a series of bands were observed, likely due to priming at stop codons within the RNA.

For the cDNA synthesis reaction, 100 ng of RNA was annealed to between 25–125 pmoles of primer mix, then extended with reverse transcriptase by standard techniques. $\alpha$-$^{32}$P-dATP was included as a trace label in the reaction. Subsequently, E. coli RNase H was added to remove the RNA strand, and an aliquot of the reaction was run on a denaturing polyacrylamide gel (FIG. 5).

A homopolymer tail of dC was added to the first strand cDNA using the enzyme terminal deoxynucleotidyl transferase. The length of the tail was controlled by including ddCTP in the extension reaction at a ratio of 1:9 with dCTP. The tailed cDNA was then copied in a second strand synthesis reaction using a primer that contained a T7 promoter followed by a 9 nucleotide dG tail, a penultimate nucleotide mix of dC/dA/dT, and a terminal random nucleotide. This primer had the following sequence (SEQ ID NO: 4; H denotes a mix of the nucleotides dA/dC/dT and N denotes a mix of all four nucleotides dG/dA/dC/dT):

5'-TAA TAC GAC TCA CTA TAG GGG GGG GGH N.

The final two nucleotides conferred priming specificity by preferentially being extended from the extreme internal portion of the homopolymer tail.

Figure 4:
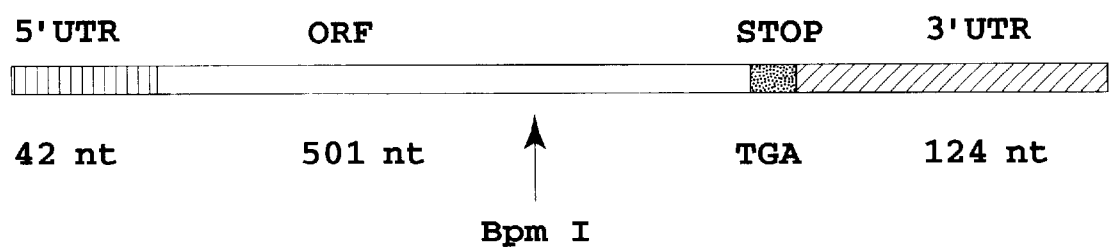
FIG. 4 is a diagram illustrating a map of the human cytochrome oxidase IV subunit A mRNA. This mRNA contains a total of 19 stop codons: one authentic codon, one in the 5' UTR, 14 in the open reading frame, and three in the 3' UTR.
Figure 6:
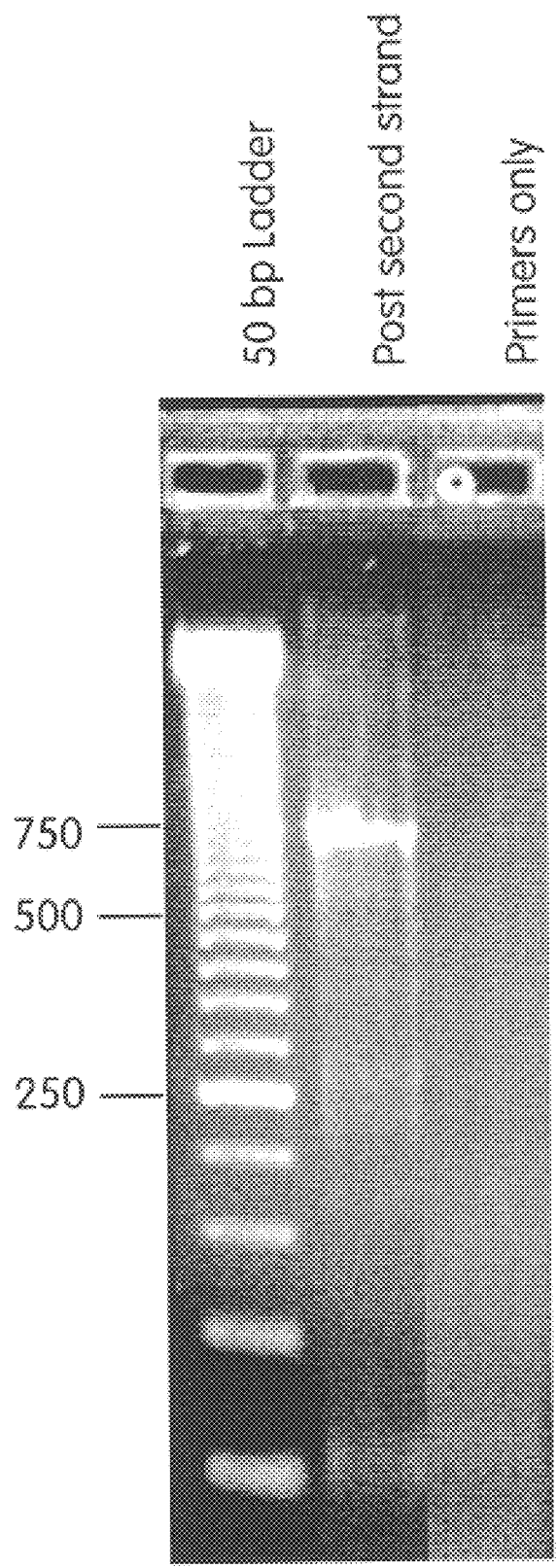
FIG. 6 is a photograph illustrating the products of second strand cDNA synthesis of the mRNA of FIG. 4. PCR amplification following second strand synthesis revealed a banding pattern similar to that observed after first strand synthesis.

After second strand synthesis, PCR (using primers complementary to the fixed regions of the primers from FIGS. 4) was used to generate a double-stranded template (FIG. 6). This template was then partially digested with Bpm I endonuclease. Cleavage from the Bpm I site in the second strand primer resulted in the removal of the third position nucleotide from all stop codons. A new double-stranded 3' terminus encoding the affinity sequence Strep-Tag II (available from Genosys Biotechnologies, Inc., The Woodlands, Tex.) was then ligated onto the cleaved fragments. This new terminus was designed to be ligated in frame with the authentic stop codon, converting it to a tyrosine and thus eliminating the stop.

Figure 7:
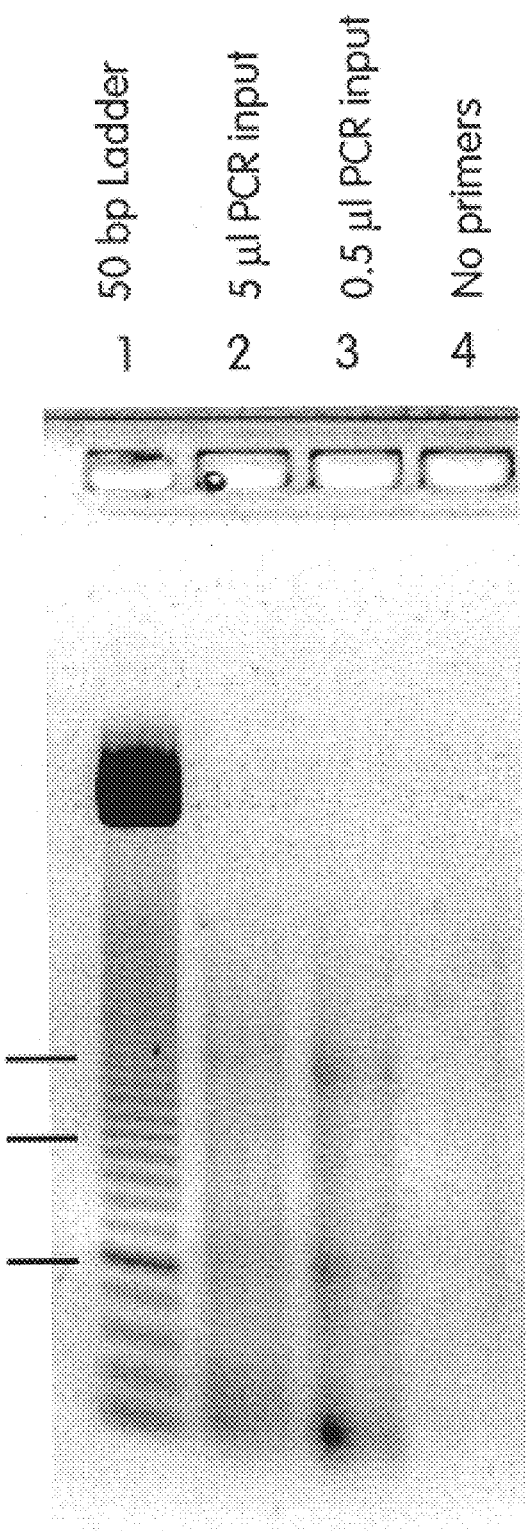
FIG. 7 is a photograph illustrating the products of an in vitro transcription reaction using the cDNA of FIG. 6 and "pull through" PCR following ligation of the affinity tag 3' terminus. The image shown is color reversed from an ethidium stained agarose gel to enhance resolution.

After ligation, a PCR reaction was performed using a primer that annealed to the new 3' terminus. Thus, only successfully ligated templates were amplified. As shown in FIG. 7, a number of products were amplified, resulting in a pattern similar to that observed in FIG. 6. One additional major product was observed at ~250 nucleotides as was expected from partial cleavage at the internal BpmI site.

Figure 8:
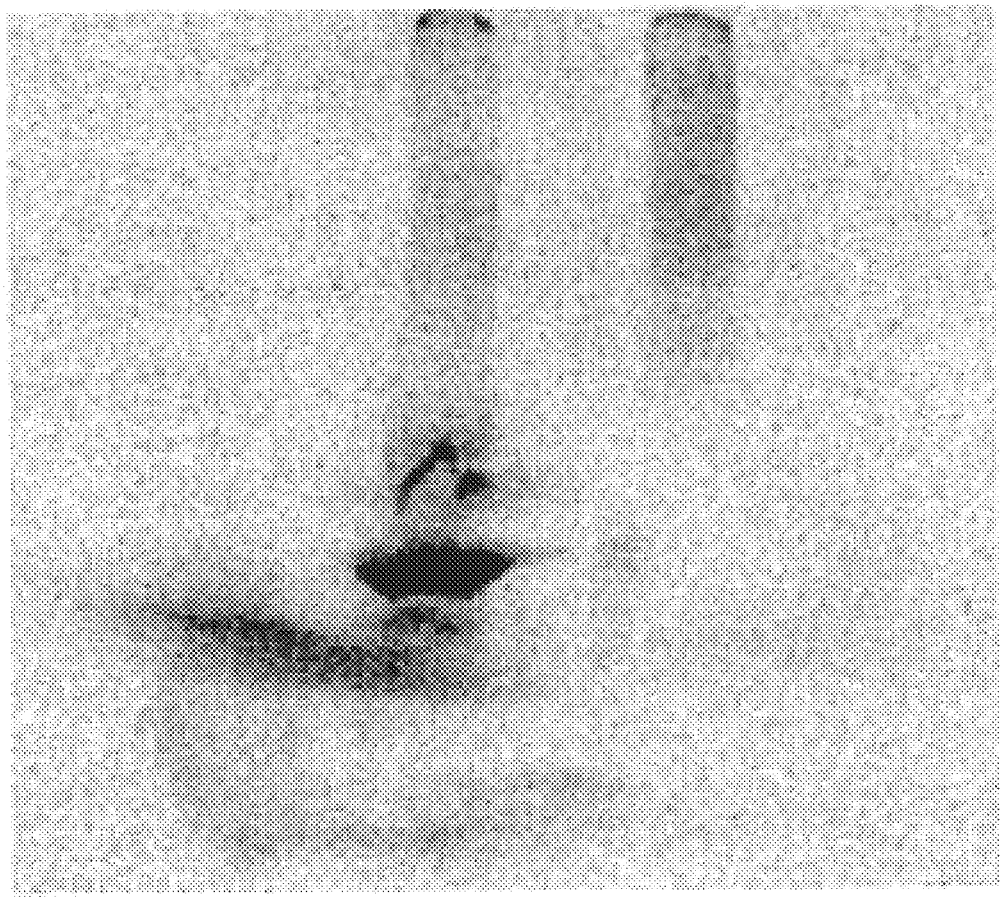
FIG. 8 is a photograph illustrating RNA-protein fusions produced from cellular mRNA using biased random priming to remove stop codons.

The double-stranded template from FIG. 7 was used in a transcription reaction to produce RNA (as described in Roberts & Szostak (1997) Proc. Natl. Acad. Sci. USA 94, 12297–12302; and Szostak et al., Selection of Proteins Using RNA-Protein Fusions, U.S. Ser. No. 09/007,005, Jan. 14, 1998, and U.S. Ser. No. 09/247,190, Feb. 9, 1999). The RNA was then enzymatically ligated to a puromycin-containing DNA linker (by the method of Roberts & Szostak (1997) Proc. Natl. Acad. Sci. USA 94, 12297–12302; and Szostak et al., Selection of Proteins Using RNA-Protein Fusions, U.S. Ser. No. 09/007,005, Jan. 14, 1998, and U.S. Ser. No. 09/247,190, Feb. 9, 1999) and placed in a translation reaction containing $^{35}$S-methionine. After translation and a subsequent high-salt fusion formation step (as described in Szostak et al., Selection of Proteins Using RNA-Protein Fusions, U.S. Ser. No. 09/247,190, Feb. 9, 1999), the RNA and fused protein were purified using oligo-dT cellulose (FIG. 8). The resulting library of RNA-protein fusion molecules indicated that the present method very efficiently generated such fusions beginning with an mRNA starting material.

Finally, in a fourth general approach, random priming is used to remove both 3' untranslated regions and stop codons from cDNA molecules. The methods described above for producing fusions from cellular RNA are generally designed to produce protein moieties with essentially wild-type N-termini. However, it is sometimes advantageous to create libraries of fusions from cellular RNA that consist of various N- and C-terminal truncated species as well. For example, such a domain library may contain functional units that are easier to produce and select than full-length proteins. To generate such a library, random priming was utilized to generate cDNA molecules as follows.

Poly A$^+$ mRNA was obtained by standard methods from two sources, human bone marrow and HL60 cells. A cDNA copy of this mRNA was then produced using the following primer (SEQ ID NO: 5):

5' GC CTT ATC GTC ATC GTC CTT GTA GTC GAA ACT AGA NNN NNN NNN.

Figure 9:
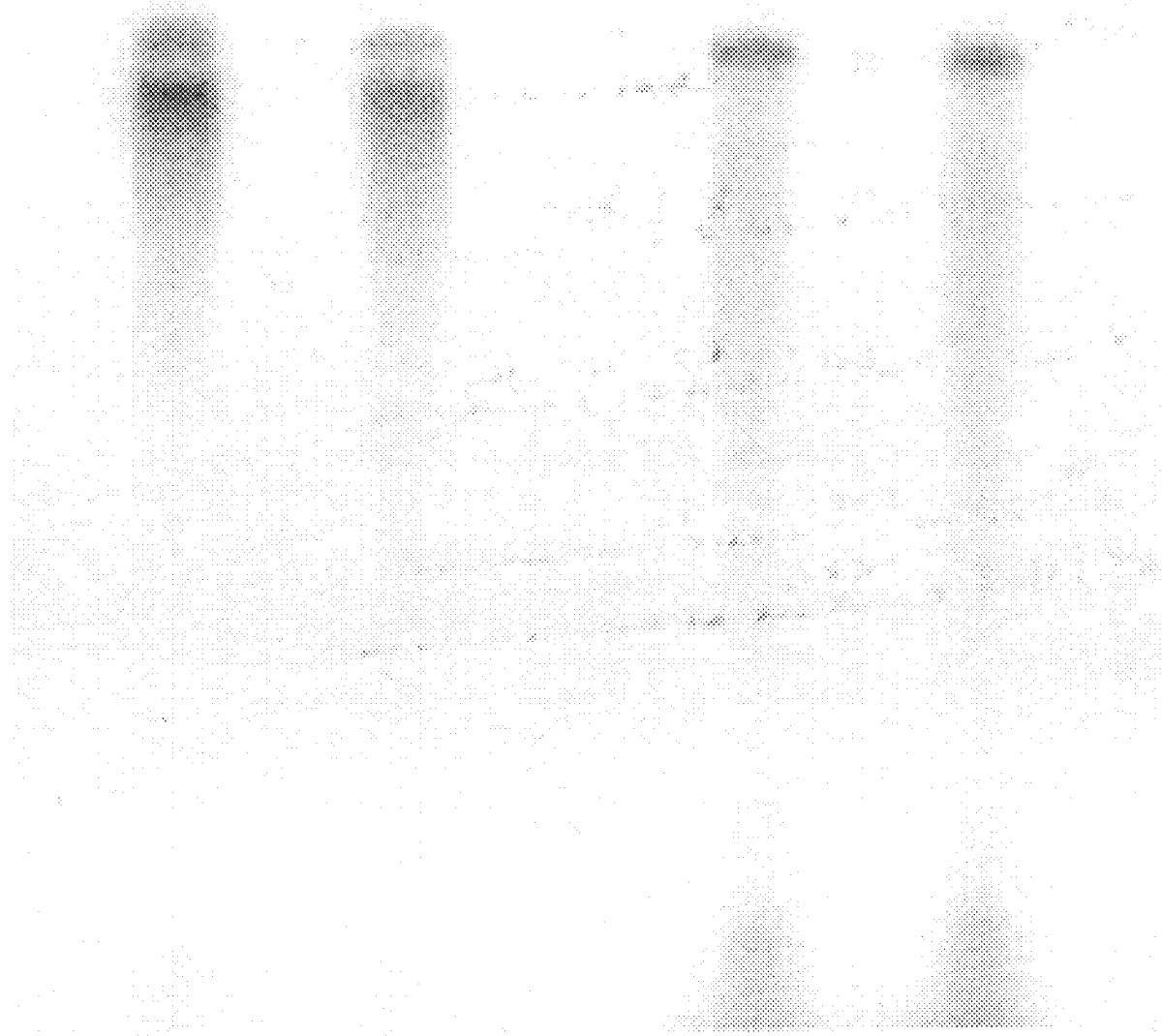
FIG. 9 is a photograph showing the products of random primed cDNA synthesis from polyA+ mRNA from HL60 cells and normal human bone marrow (NBM) run on a denaturing acrylamide gel.

This first strand primer was in the minus sense relative to the RNA strand and in one reading frame encoded the FLAG epitope. Because this fixed sequence contained no stop codons in two of the three potential reading frames, RNA produced from this template would contain no stop codons in two reading frames. This primer contained a 5' fixed sequence and nine random nucleotides at the 3' terminus. 125 pmoles of the primer was annealed to 5 μg of mRNA and then extended using reverse transcriptase and standard techniques. A portion of the reaction was performed in the presence of α-$^{32}$P-dATP as a tracer and assayed by denaturing gel electrophoresis (FIG. 9). After first strand synthesis, the RNA strand was removed by digestion with RNase H. Unextended primers were removed by size exclusion chromatography.

Second strand cDNA synthesis was performed using the Klenow fragment of DNA polymerase and the following primer (SEQ ID NO: 6):

5' GGA CAA TTA CTA TTT ACA ATT ACA ATG NNN NNN NNN

This second strand primer was in the plus sense relative to the RNA strand, contained nine random nucleotides at the 3' end, and included a 5' fixed region having an ATG start codon and the 5' UTR from tobacco mosaic virus as a ribosome binding site. Again, a portion of the reaction was performed in the presence of α-$^{32}$P-dATP as a tracer (FIG. 9). The unextended primers were removed by size exclusion chromatography.

Figure 10:
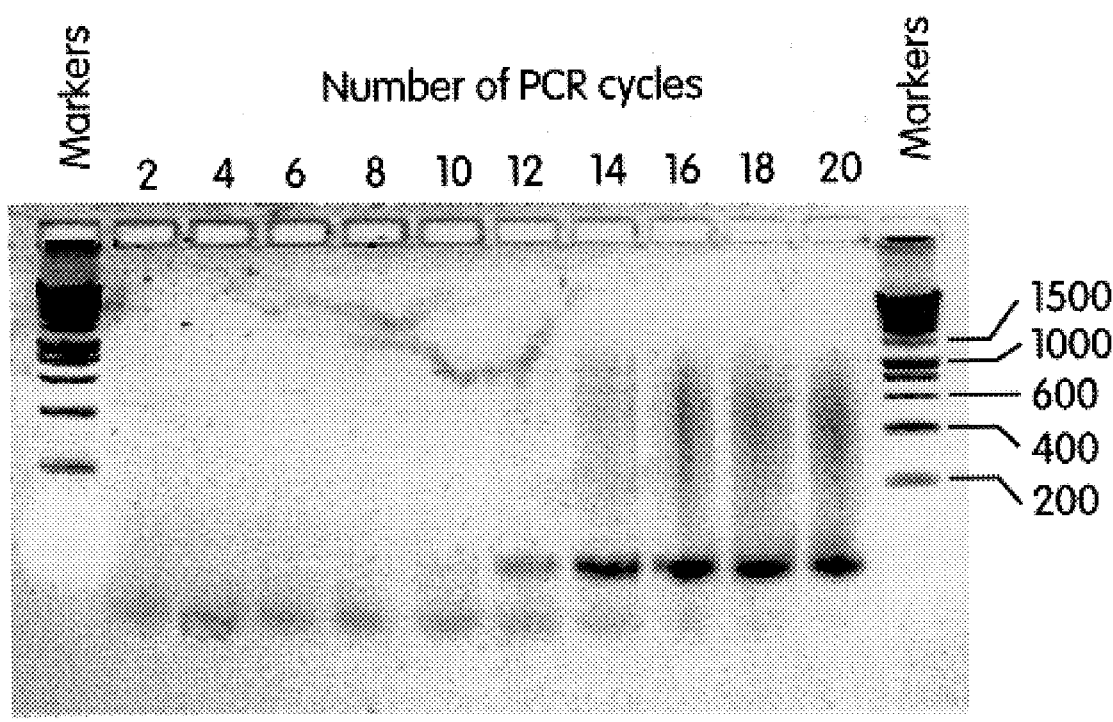
FIG. 10 is a photograph illustrating PCR-amplified second strand cDNA generated from the product of FIG. 9. An aliquot of the second strand synthesis reaction was PCR amplified under standard conditions. Aliquots were removed after the specified number of cycles and run on a 2% agarose gel. The image shown is a negative of the ethidium stained gel to enhance resolution.

The second strand cDNA containing both fixed regions was then amplified by PCR to create a double stranded template (FIG. 10). The forward PCR primer was complementary to the 5' UTR region of the second strand primer and also encoded the promoter sequence for T7 RNA polymerase. The reverse PCR primer was complementary to the fixed region of the first strand primer and also encoded sequences required for subsequent ligation of RNA produced from the template. These primer sequences are shown below (SEQ ID NOS: 7, 8):

5' TAA TAC GAC TCA CTA TAG GGA CAA TTA CTA TTT ACA ATT (forward)

5' AGA AGA TGC GCG ATC GTC ATC GTC CTT GTA GTC (reverse).

Figure 11:
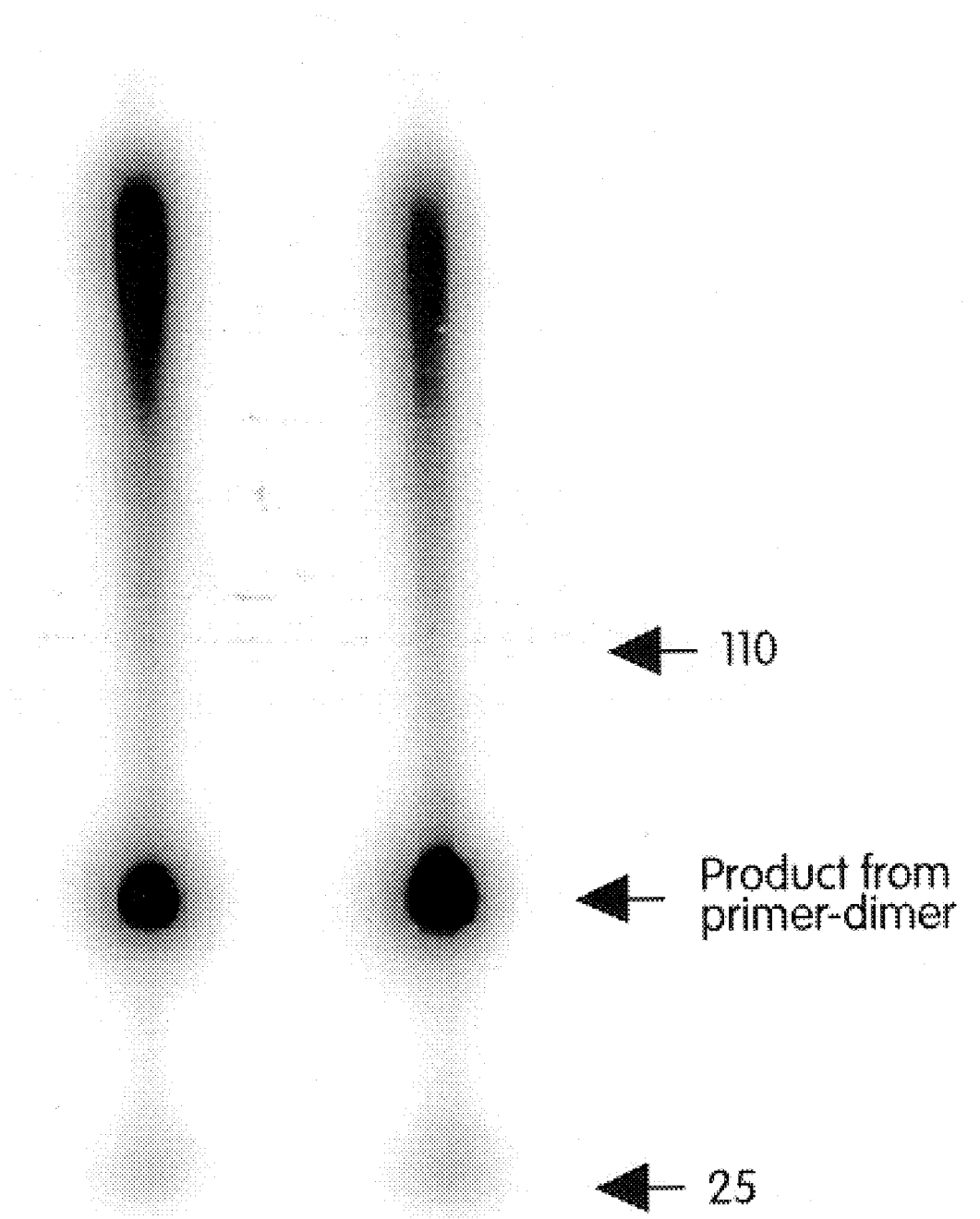
FIG. 11 is a photograph illustrating radiolabeled RNA transcripts produced from the dsDNA template library of FIG. 10. These transcripts were produced using T7 RNA polymerase and run on a denaturing polyacrylamide gel.

The results of this amplification step are shown in FIG. 10. The intense PCR product of approximately 75 nucleotides (FIG. 10) was apparently due to primer-dimer formation and could be reduced with an additional size exclusion chromatography step. The double-stranded template from PCR was transcribed using T7 RNA polymerase (as described in Roberts & Szostak (1997) Proc. Natl. Acad. Sci. USA 94, 12297–12302; and Szostak et al., Selection of Proteins Using RNA-Protein Fusions, U.S. Ser. No. 09/007,005, Jan. 14, 1998, and U.S. Ser. No. 09/247,190, Feb. 9, 1999). When α-$^{32}$P-dATP was included in the transcription reaction a range of RNA transcripts was produced that reflected the variable size of the template library (FIG. 11). Because the specific activity of a given transcript was proportional to the length, longer RNA products appeared darker.

Figure 12:
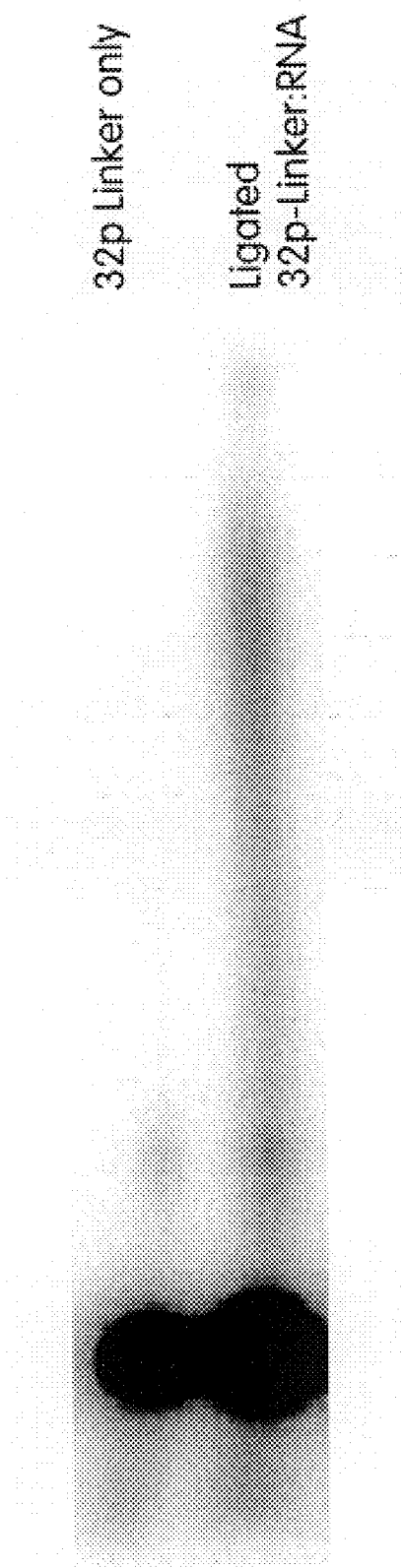
FIG. 12 is a photograph illustrating that ligation of a $^{32}$P-labeled linker to the RNA library of FIG. 11 results in a shift in mobility of the linker.

A parallel transcription reaction was performed without a radioactive tracer and the resulting RNA was purified by phenol/chloroform extraction and size exclusion chromatography. A DNA linker with a 5' puromycin moiety was then ligated to the end of the RNA in a template directed reaction using T4 DNA ligase (as described in Roberts & Szostak (1997) Proc. Natl. Acad. Sci. USA 94, 12297–12302; and Szostak et al., Selection of Proteins Using RNA-Protein Fusions, U.S. Ser. No. 09/007,005, Jan. 14, 1998, and U.S. Ser. No. 09/247,190, Feb. 9, 1999). The DNA linker was 5' radiolabeled with $^{32}$P to allow the reaction to be followed on a denaturing polyacrylamide gel (FIG. 12). The shift in mobility of the linker was the result of ligation to the RNA library.

Figure 13:
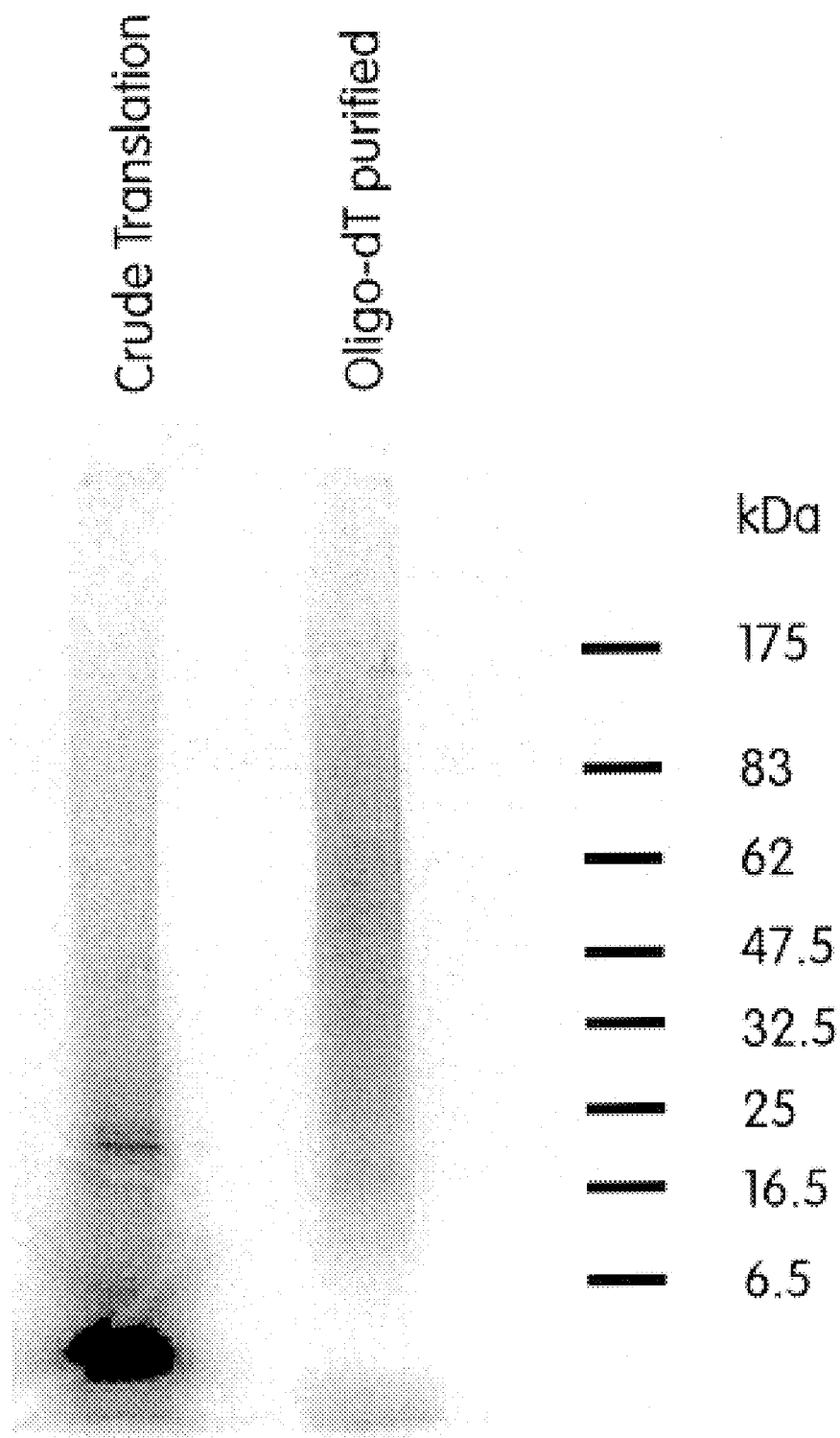
FIG. 13 is a photograph illustrating fusions formed between the RNA library of FIG. 11 and translated peptides. These fusions were purified by oligo-dT cellulose and analyzed by SDS-PAGE. Such fusions could only be formed in the absence of a stop codon.

The ligated RNA was then purified from unligated RNA and linker, and incubated in an in vitro translation system to generate protein-RNA fusions (by the methods of Roberts & Szostak (1997) Proc. Natl. Acad. Sci. USA 94, 12297–12302; and Szostak et al., Selection of Proteins Using RNA-Protein Fusions, U.S. Ser. No. 09/007,005, Jan. 14, 1998, and U.S. Ser. No. 09/247,190, Feb. 9, 1999). The translation reaction contained $^{35}$S-met so that the newly translated proteins were radiolabeled. After fusion formation, the resultant complexes were purified using oligo-dT cellulose, and an aliquot was analyzed by SDS-PAGE (FIG. 13). If an RNA being translated contained a stop codon, the ribosome complex would dissociate from the template, and no fusion would be formed. Accordingly, the formation of fusions correlated with the lack of stop codons.

A fusion library constructed essentially as above was subsequently selected for a particular aspect of the protein portion of the protein-RNA fusion. A number of individual members of the resulting selected pool were isolated and sequenced (FIG. 14). Alignment with the parental RNA sequences obtained from a sequence database allowed the selected region to be identified. Comparison of the recovered clones with the parent RNA showed that, in general, each of these clones represented an in-frame region of a cellular RNA message devoid of both stop codons and a 3' UTR.

EXAMPLE 2

Neutralization or Removal of Release Factors

In a second general approach of the invention, stop codons present in an RNA sequence are overcome by neutralization or removal of translation release factors from in vitro translation mixes. To inhibit polypeptide chain release in a eukaryotic translation system, either or both of the two eukaryotic release factors, eRF1 and eRF3, must be neutralized. In prokaryotic translation systems, both RF1 and RF2 or, alternatively, RF3 alone must be neutralized to inhibit polypeptide chain release. In either case, a release factor is neutralized by the use of antibodies or by exploiting genetically engineered variants of the natural release factor binding partners. Alternatively, the release factor may be removed from the translation mix by using its affinity to specific components of the translation complex, such as stop codons.

Neutralizing antibodies, which can be either polyclonal or monoclonal, are raised against the entire release factor or to one of its constituent domains or peptides. One such antibody and an exemplary method of preparation is described in Zhouravleva et al. (EMBO J. 14:4065–72 (1995)). Such antibodies may be produced by any standard technique. Preferably, the antigen is first expressed in a heterologous expression system or synthesized chemically and then purified to homogeneity. The antigenic peptide may be coupled to a carrier protein, such as KLH as described in Ausubel et al, Current Protocols in Molecular Biology, Wiley Interscience, New York, N.Y. The peptide may then be mixed with Freund's adjuvant and injected into guinea pigs, rats, or preferably rabbits to produce polyclonal antibodies. The antibodies may be purified by peptide antigen affinity chromatography. Monoclonal antibodies may be prepared using these same antigenic peptides and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra).

Alternatively, natural release factor-binding partners may be exploited as inhibitors. Exemplary binding partners include other release factors and components of the translation termination complex. For example, eRF1 may be neutralized by an excess of an inactive mutant of eRF3. Conversely, eRF3 may be neutralized by an inactive mutant of eRF1. Similarly, RF1 and RF2 can both be inhibited by an excess of an inactive mutant of RF3, and RF3 can be inhibited by an excess of an inactive mutant of RF1 or RF2. Such mutants are created by standard techniques, for example, by random or site-directed mutagenesis, followed by an assay for loss of RF activity; in one particular example, residues in the GTP-binding motif of RF3 necessary for activity may be mutated. Alternatively, analogues of stop codons may be used as inhibitors to bind, for example, to RF1. Exemplary stop codon analogues are short oligonucleotides (composed of RNA, DNA, or chemically modified RNA) which contain the sequence of all possible stop codons.

Any of the above described release factor inhibitors may be used in at least three different ways. First, as described above, a soluble inhibitor may be added to an in vitro translation mixture. Upon addition, the inhibitor binds tightly to its target and prevents the release factor from interacting with the mRNA protein-ribosome-GTP complex. Alternatively, the inhibitor (including a stop codon sequence) may be immobilized on a solid bead. Following the addition of immobilized inhibitor to the translation mixture, the inhibitor binds to the release factor, and the complex of release factor and immobilized inhibitor are removed from solution, for example, by centrifugation or microfiltration. In yet another alternative, the inhibitor may be immobilized on a column, and the translation mixture passed through the column. The translation mixture that flows through the column is cleared of release factor and, when used as an in vitro translation mix, fails to release a nascent polypeptide chain from an mRNA-ribosome-GTP complex.

All patents and publications mentioned herein are hereby incorporated by reference.

Other embodiments are within the claims.

What is claimed is:

1. A method for removing the 3'-untranslated regions and stop codons of a population of mRNA molecules, said method comprising:
   (a) providing a population of mRNA molecules;
   (b) synthesizing strands of DNA, each of which is complementary to one of said mRNA molecules, using a random primer mixture, said random primer mixture comprising primers, each having
      (i) a 3' region comprising a stop codon flanked by a random oligonucleotide located 3', 5', or both to said stop codon; and
      (ii) a 5' region comprising a Type IIS restriction site;
   (c) ligating to the 3' ends of the DNA products of step (b) an oligonucleotide tail;
   (d) amplifying the products of step (c) using
      (i) a first primer which is complementary to said Type IIS restriction site-containing sequence; and
      (ii) a second primer which is complementary to said oligonucleotide tail; and
   (e) treating the products of step (d) with said Type IIS restriction enzyme to cleave said products, thereby removing the 3'-untranslated regions and stop codons.

2. The method of claim 1, wherein said second primer of step (d) further includes a 5' region comprising an RNA polymerase recognition site.

3. The method of claim 2, wherein said method further comprises:
   (f) ligating a sequence which encodes an affinity tag to the cleaved ends of the products of step (e);
   (g) transcribing said products of step (f);
   (h) ligating peptidyl acceptors to the 3' ends of the RNA products of step (g);
   (i) translating said products of step (h) to produce a population of RNA-protein fusions; and
   (j) isolating RNA-protein fusions which comprise said affinity tag, thereby obtaining a population of mRNA molecules lacking 3'-untranslated regions and stop codons.

4. The method of claim 3, wherein said RNA polymerase recognition site is a T7 or SP6 RNA polymerase recognition site.

5. The method of claim 3, wherein said affinity tag is a hexahistidine peptide, a streptavidin-binding peptide, or an epitope.

6. The method of claim 3, wherein said peptidyl acceptor is puromycin.

7. The method of claim 1, wherein said method is carried out on a population of mRNA molecules.

8. A method for removing the 3'-untranslated regions and stop codons of a population of mRNA molecules, said method comprising:
   (a) providing a population of mRNA molecules;
   (b) synthesizing strands of DNA, each of which is complementary to one of said mRNA molecules, using a random primer mixture, said random primer mixture comprising primers, each having (i) a 5' region which lacks a stop codon in at least one reading frame and (ii) a random 3' region; and
   (c) synthesizing strands of DNA complementary to said DNA strands of step (b), using a second random primer mixture.

9. The method of claim 8, wherein said second random primer mixture comprises primers, each having (i) a 5' region which comprises a translation start site and (ii) a random 3' region.

10. The method of claim 9, wherein said method further comprises
    (d) amplifying said product of step (c) using a first amplification primer having (i) a 5' sequence which comprises an RNA polymerase recognition site and (ii) a 3' region which is complementary to said translation start site.

11. The method of claim 8, wherein said method is carried out on a population of mRNA molecules.

* * * * *

SEQUENCE LISTING

```
<160> NUMBER OF SEQ ID NOS: 20

<210> SEQ ID NO 1
<211> LENGTH: 27
<212> TYPE: DNA
<213> ORGANISM: Artificial Sequence
<220> FEATURE:
<223> OTHER INFORMATION: Synthetic random primer
<220> FEATURE:
<221> NAME/KEY: variation
<222> LOCATION: (1)...(27)
<223> OTHER INFORMATION: n is a, c, t, or g.

<400> SEQUENCE: 1
gcttgctgga gtgcgagtnn nnnncta                                            27

<210> SEQ ID NO 2
<211> LENGTH: 27
<212> TYPE: DNA
<213> ORGANISM: Artificial Sequence
<220> FEATURE:
<223> OTHER INFORMATION: Synthetic random primer
<220> FEATURE:
<221> NAME/KEY: variation
<222> LOCATION: (1)...(27)
<223> OTHER INFORMATION: n is a, c, t, or g.

<400> SEQUENCE: 2
gcttgctgga gtgcgagtnn nnnntta                                            27

<210> SEQ ID NO 3
<211> LENGTH: 27
<212> TYPE: DNA
<213> ORGANISM: Artificial Sequence
<220> FEATURE:
<223> OTHER INFORMATION: Synthetic random primer
<220> FEATURE:
<221> NAME/KEY: variation
<222> LOCATION: (1)...(27)
<223> OTHER INFORMATION: n is a, c, t, or g.

<400> SEQUENCE: 3
gcttgctgga gtgcgagtnn nnnntca                                            27
```

```
<210> SEQ ID NO 4
<211> LENGTH: 28
<212> TYPE: DNA
<213> ORGANISM: Artificial Sequence
<220> FEATURE:
<223> OTHER INFORMATION: Synthetic random primer
<220> FEATURE:
<221> NAME/KEY: variation
<222> LOCATION: (1)...(28)
<223> OTHER INFORMATION: n is a, c, t, or g.
<220> FEATURE:
<221> NAME/KEY: variation
<222> LOCATION: (1)...(28)
<223> OTHER INFORMATION: h is a or c or t/u;

<400> SEQUENCE: 4
taatacgact cactataggg gggggghn                                    28

<210> SEQ ID NO 5
<211> LENGTH: 44
<212> TYPE: DNA
<213> ORGANISM: Homo sapiens
<220> FEATURE:
<221> NAME/KEY: variation
<222> LOCATION: (1)...(44)
<223> OTHER INFORMATION: n is a, c, t, or g.

<400> SEQUENCE: 5
gccttatcgt catcgtcctt gtagtcgaaa ctagannnnn nnnn                  44

<210> SEQ ID NO 6
<211> LENGTH: 36
<212> TYPE: DNA
<213> ORGANISM: Homo sapiens
<220> FEATURE:
<221> NAME/KEY: variation
<222> LOCATION: (1)...(36)
<223> OTHER INFORMATION: n is a, c, t, or g.

<400> SEQUENCE: 6
ggacaattac tatttacaat tacaatgnnn nnnnnn                           36

<210> SEQ ID NO 7
<211> LENGTH: 39
<212> TYPE: DNA
<213> ORGANISM: Phage T7

<400> SEQUENCE: 7
taatacgact cactataggg acaattacta tttacaatt                        39

<210> SEQ ID NO 8
<211> LENGTH: 33
<212> TYPE: DNA
<213> ORGANISM: Homo sapiens

<400> SEQUENCE: 8
agaagatgcg cgatcgtcat cgtccttgta gtc                              33

<210> SEQ ID NO 9
<211> LENGTH: 36
<212> TYPE: DNA
<213> ORGANISM: Homo sapiens

<400> SEQUENCE: 9
gtgtatgggt tgtttatgac aatttatgaa atgacg                           36
```

-continued

```
<210> SEQ ID NO 10
<211> LENGTH: 36
<212> TYPE: DNA
<213> ORGANISM: Homo sapiens

<400> SEQUENCE: 10
gcgtatgggt tgtttatgac aatttatgaa atacag                          36

<210> SEQ ID NO 11
<211> LENGTH: 36
<212> TYPE: DNA
<213> ORGANISM: Homo sapiens

<400> SEQUENCE: 11
aaagttgttc aagtttatcc agagtttggg cagaag                          36

<210> SEQ ID NO 12
<211> LENGTH: 36
<212> TYPE: DNA
<213> ORGANISM: Homo sapiens

<400> SEQUENCE: 12
aaagttgttc aagtttatcc agagtttgag caggaa                          36

<210> SEQ ID NO 13
<211> LENGTH: 36
<212> TYPE: DNA
<213> ORGANISM: Homo sapiens

<400> SEQUENCE: 13
ggtaacacac agaggaaaga tattgtcctg gatgta                          36

<210> SEQ ID NO 14
<211> LENGTH: 36
<212> TYPE: DNA
<213> ORGANISM: Homo sapiens

<400> SEQUENCE: 14
ggtaacacac agaggaaaga tattgtccgg gatgga                          36

<210> SEQ ID NO 15
<211> LENGTH: 36
<212> TYPE: DNA
<213> ORGANISM: Homo sapiens

<400> SEQUENCE: 15
ttggttttgg atgaagctag gtacctgcct ccagcc                          36

<210> SEQ ID NO 16
<211> LENGTH: 36
<212> TYPE: DNA
<213> ORGANISM: Homo sapiens

<400> SEQUENCE: 16
ttggttttgg atgaagctag gtacctgcct ccagcc                          36

<210> SEQ ID NO 17
<211> LENGTH: 36
<212> TYPE: DNA
<213> ORGANISM: Homo sapiens

<400> SEQUENCE: 17
ggtggagaga cctacaccga tcctgattta cacacc                          36
```

```
<210> SEQ ID NO 18
<211> LENGTH: 35
<212> TYPE: DNA
<213> ORGANISM: Homo sapiens

<400> SEQUENCE: 18
ggtggagaga cctacaccga tcctgatcta catca                           35

<210> SEQ ID NO 19
<211> LENGTH: 36
<212> TYPE: DNA
<213> ORGANISM: Homo sapiens

<400> SEQUENCE: 19
ggtctctatt ttacccccac aggcttccac ggacat                          36

<210> SEQ ID NO 20
<211> LENGTH: 36
<212> TYPE: DNA
<213> ORGANISM: Homo sapiens

<400> SEQUENCE: 20
ggtctctatt ttaccctcac aggcttccac ggactt                          36
```